United States Patent [19]

Sijmons et al.

[11] Patent Number: 5,650,307
[45] Date of Patent: Jul. 22, 1997

[54] PRODUCTION OF HETEROLOGOUS PROTEINS IN PLANTS AND PLANT CELLS

[75] Inventors: Peter Christiaan Sijmons, Amsterdam; Andreas Hoekema, Oegstgeest; Bernardus Martinus M. Dekker, Gouda; Barbara Schrammeijer, Rotterdam; Teunis Cornelius Verwoerd, Leiden; Peturs Josephus M. Van Den Elzen, Voorhout, all of Netherlands

[73] Assignee: Mogen International, n.v., Leiden, Netherlands

[21] Appl. No.: 469,856

[22] Filed: Jun. 6, 1995

Related U.S. Application Data

[63] Continuation of Ser. No. 659,287, filed as PCT/NL90/00108, Jul. 26, 1990.

[30] Foreign Application Priority Data

Jul. 26, 1989 [NL] Netherlands ............................ 8901932
Jul. 26, 1990 [WO] WIPO ...................... PCT/NL90/00108

[51] Int. Cl.$^6$ ........................... C12N 15/63; C12N 15/82; A01H 5/00; C07K 14/765
[52] U.S. Cl. ................... 435/172.3; 435/69.1; 435/70.1; 800/205; 800/250; 800/255; 800/DIG. 42; 800/DIG. 43; 530/363; 530/387.3; 47/58
[58] Field of Search ..................... 800/205, 250, 800/255, DIG. 42, DIG. 43; 435/172.3, 69.1, 69.6, 69.8, 70.1, 240.2; 530/363, 387.3; 935/10, 11, 35, 67; 47/58

[56] References Cited

U.S. PATENT DOCUMENTS 4,956,282  9/1990  Goodman et al. .................... 435/69.51

FOREIGN PATENT DOCUMENTS 0091527  10/1983  European Pat. Off. ........ C12N 15/00

OTHER PUBLICATIONS

C. Dorel et al., J. Cell Biol., vol. 108 (Feb. 1989) pp. 327–337.
G. Iturriaga et al., The Plant Cell, vol. 1 (Mar. 1989) pp. 381–390.
C. Dorel et al. (Abstract) Plant Physiology, vol. 86 (4 Suppl.) (88) p. 84.

*Primary Examiner*—Charles C. P. Rories
*Attorney, Agent, or Firm*—Morrison & Foerster LLP

[57] ABSTRACT

This invention provides for a method to produce excreted and correctly processed heterologous protein-material in a plant host. The method comprises the step of transforming a plant host using a recombinant polynucleotide, which comprises the DNA sequences encoding the fully processed heterologous protein material, directly preceded by a DNA sequence coding for a plant signal peptide, and regulatory sequences necessary for the plant host to express the heterologous gene construct, resulting in excretion of the heterologous protein from the cell and correct cleavage of the N-terminal signal peptide, so that the mature heterologous protein produced by the plant host is identical to the corresponding protein produced in its authentic host.

9 Claims, 5 Drawing Sheets

PRODUCTION OF HETEROLOGOUS PROTEINS IN PLANTS AND PLANT CELLS

CROSS-REFERENCES TO RELATED APPLICATIONS

This application is a continuation of application Ser. No. 07/659,287 filed 21 May 1991, which is the U.S. national phase of PCT/NL90/00108 filed 26 Jul. 1990.

FIELD OF THE INVENTION

The present invention is in the field of recombinant DNA technology, more in particular recombinant DNA technology concerning the genetic manipulation of plants and is related to a process for the production of proteins or polypeptides using genetically manipulated plants or plant cells, as well as to the genetically manipulated plants and plant cells per se (including parts of the genetically manipulated plants), the heterologous protein material (e.g. a protein, polypeptide and the like) which is produced with the aid of these genetically manipulated plants or plant cells, and the recombinant polynucleotides (DNA or RNA) that are used for the genetic manipulation.

STATE OF THE ART

One of the results of biotechnology is the development of new production methods for proteins. In virtue of this, it is possible to accomplish that, on a preparative scale, microorganisms containing recombinant DNA produce proteins which these microorganisms naturally do not synthesize, or naturally do not synthesize in those quantitities. Recent examples are in particular insulin, various interferon types and human growth hormone that are produced in commercial quantities by, among others, bacteria and yeast cells.

Characteristic for these examples is the fact that this often concerns relatively simple polypeptides that do not require co- or post-translational processing within the cell, to obtain their final form and biological function. For a large number of more complex proteins of higher organisms, such a processing is of concern for the functioning of those proteins. For example, they need to be correctly glycosylated or undergo a membrane passage during which signal peptides are split off from a precursor ('precursor-protein'). In prokaryotic microorganisms this is not possible, due to which higher organisms such as fungi have to be used.

Proteins synthesized on the rough endoplasmatic reticulum (ER) are excreted by the eukaryotic cell or stored at specific locations in the excretion route like the ER, Golgi complex, plasma membrane or vacuole/lysosome (Pfeffer & Rothman, 1987). The choice of the excretion route is determined by the presence of a hydrophobic, amino-terminal signal peptide that is cleaved off from the precursor-protein. Examples of this are signal peptides for invertase (Carlston & Botstein, 1982) or α-factor (Herskowitz & Oshima, 1982) that cause the respective mature protein products to reach the periplasmic space. Recently it was shown that signal peptides can also be used to achieve excretion of human proteins by yeast cells, although in that case processing is not complete (Stetler et al., 1989).

From the experiments with the synthesis of animal proteins in fungi, it appeared that the use of fungal signal peptides gives more efficient processing and excretion than animal signal peptides, which means that a signal peptide, derived from the fungus which is acting as host, is functioning better (Kingsman et al., 1987; Harkki et al., 1989).

For the transport to the lysosomes in mammals (Kornfeld., 1987), or vacuoles in yeast (Johnsson et al., 1987) and plant cells (Dorel et al., 1989) additional information is required that is located in part of the sequence of the mature protein itself.

The knowledge of signal peptides for the excretion by plant cells is still very limited (Della-Cioppa et al., 1987). Such signal peptides have only been described for 2 extensins from carrot (Chen & Varner, 1985) and tobacco (memelink, 1988), as well as for three pathogenesis-related (PR) proteins from tobacco (Hooft van Huijsduijnen et al., 1985; Cornelissen et al., 1986); De Loose et al., 1988). From this small number of signal peptides no consensus has been obtained on the characteristics of cleavage- or recognition-sites. Neither has it become clear whether proteins, that are foreign to the plant, can be excreted by plant cells, nor if the processing of the signal peptide occurs correctly when a fusion construct between a plant signal peptide and a heterologous protein would be used.

It has nevertheless been shown that plants are also a candidate as a production system for heterologous proteins. However, till now only the production of non-complex proteins in plants has been shown (Goodman et al., 1987; Misra, 1989).

EP-A-0 255 153 describes the isolation and identification of a gene encoding a pre-pro form of an alpha-galactosidase from guar seed. Said gene may be expressed by other plants, such as tobacco plants. It is concluded from Western blotting results, mobility determinations and observation of alpha-galactosidase activity in culture supernatants that the pre-pro form of alpha-galactosidase, as encoded by the transferred gene, is secreted and correctly processed to the mature form when expressed by tobacco callus.

This reference teaches that a plant gene, if transferred as a whole, including its own pre-pro sequences, into another plant species, may be expressed, secreted and correctly processed therein. It does not teach, however, whether less related genes, such as genes of animal or human origin, may be expressed, secreted and correctly processed in plants.

The expression of a heterologous gene in plant cells is disclosed in EP-A-0 270 248, which describes a DNA construct comprising a downstream coding sequence preceded by an upstream base sequence. The downstream coding sequence codes for a protein which is desired to be transported to a plant cell wall. The bacterial beta-glucuronidase gene is used as a model gene, because its expression can be directly detected. The upstream base sequence codes for a cell wall targeting protein consisting of the leader sequence (or part of it) of the polygalacturonase precursor. Said polygalacturonase (PG) is an enzyme of plant origin which is involved in the ripening of climacteric fruit. Two kinds of DNA constructs are disclosed in this reference: one contains a DNA fragment encoding the complete leader of PG and the first six amino acids of the mature PG protein as the upstream base sequence, the other construct contains only a part of the PG leader sequence as the upstream base sequence; the last 22 codons of the PG leader sequence are missing.

The reference does not show whether the fusion protein is secreted and processed correctly, i.e. cleaved at the correct cleavage site. It is conceivable that excretion and even some form of processing occur, but it does not seem likely that the processing will be fully correct.

The use of an upstream base sequence encoding a signal peptide of plant origin for obtaining secretion of a bacterial protein by transformed plant cells is suggested also by Passiatore et al., J. Cell. Biochem. Suppl. 13D, 27 Mar–7 Apr. 1989, page 267, Abstract M145, but again it is not shown whether the fusion protein is secreted and correctly processed. The exact structure of the DNA constructs, which comprise a bacterial chitinase gene preceded by extensin and proteinase inhibitor I leader sequences of plant origin, is not shown, either.

EP-A-0 307 841 relates to the regulatory sequences of the pathogenesis-related (PR) protein genes of the PR-1 group and discloses an inducible PR-1 promoter and PR-1 secretion signal sequences. It is suggested that the PR-1 signal sequences may be used to regulate in plants the secretion of heterologous proteins. However, it is not shown that such fusions are indeed functional. At that time it was far from predictable whether the combination of mature sequences and signal sequences from very divergent systems (such as plants and humans) would indeed give rise to a correct cleavage of the signal peptide, resulting in a mature heterologous protein with exactly the same N-terminus as the wildtype protein. A correct cleavage appears to be dependent on the amino acid sequences flanking the cleavage site. Therefore, this reference does not show that, nor how, a correct processing of animal and human proteins, such as HSA, could be obtained in plants.

EP-A-0 091 527 discloses the production of HSA-like peptides in *E. Coli* as a host. Although it is suggested that other host organisms may be used, including other bacteria, yeasts, fungi, animal and plant hosts, it is also expressly stated therein that "hosts may lack the appropriate enzymes which may be required to transform the host-produced polypeptide to the structure and substitution of natural HSA". This reference also suggests quite generally that the HSA gene may be combined with various signal sequences, both prokaryotic and eukaryotic, as to permit secretion of the HSA from the cells of the transformed host. Instead of giving details and experimental evidence, however, a reference is made to Villa-Komaroff et al., "A bacterial Clone synthesizing Proinsulin", P.N.A.S. USA 75, 1978, pp. 3727-3731, and to Talmadge et al., "Eukaryotic Signal Sequence Transports Insulin Antigen in *Escherichia coli*", P.N.A.S. USA 77, 1980, pp. 3369-3373. These references do not disclose any methods of producing excreted and/or correctly processed animal proteins in a plant host, however.

Therefore, it is still unclear whether plants or plant cells are suited for the expression of heterologous proteins that require co- or post-translational processing.

DESCRIPTION OF THE INVENTION

According to the invention it was found that a heterologous, for example non-plant, protein can be excreted by transgenic plant cells using a plant signal peptide. The protein human serum albumine (HSA) has been selected as an example of a protein that during excretion requires a complex in vivo processing. HSA is the main component of blood plasma. It is a protein of 585 amino acids when it is fully processed, it contains 17 disulfide bridges (Bherens et al., 1975). In order to obtain processing, a passage across a cell membrane must take place, during which a signal peptide is cleaved off and the protein can obtain its proper folding. Proteins that are excreted by their natural host are supposed not to fold or to fold incorrectly when they are synthesised intracellularly. Excretion is a prerequisite to establish the correct folding of the disulfide bridges.

Till now, HSA is purified from blood-plasma according to a conventional method. The protein is being used in quantities in the order of grams for the replacement of blood in cases of trauma and several clinical situations. For a couple of reasons the production of HSA in a recombinant host is very attractive. In the first place to eliminate the risk of spreading infectious diseases (like AIDS and hepatitis) during HSA-treatment and in the second place to reduce the dependance on available blood. The protein HSA is synthesised intracellularly in *Escherichia coli* (Latta et al., 1987) and also expressed and excreted in *Bacillus subtilis* (Saunders and Guyer, 1987). Excretion of HSA has been proven in transgenic yeast cells of *Saccharomyces cerevisiae* (Etcheverry et al., 1986).

According to the invention plant signal peptides are used, in particular those obtained from PR-proteins, in fusion constructs with especially non-plant proteins for the production of extracellular proteins in plants or plant cell cultures. As an example of a useful plant signal peptide, a signal peptide was used derived from the thaumatin-like PR-protein, encoded by PROB12 from tobacco (Cornelissen 1986), coding for a hydrophobic N-terminal peptide of 24 amino acids.

According to the invention a plant signal peptide can be used for the following goals:

a) production in plants or plant cells of proteins that require processing for their physiological action (for instance human serum albumine), b) production in plants or plant cells of proteins that require excretion for economical or process-technical reasons (for example for the cheap isolation from the culture medium of the suspension cells), c) production of proteins that need to have their function in the extracellular space (for example for the introduction of genes coding for proteins that provide the plant with resistance against pathogens that invade via the extracellular spaces or colonize said spaces).

On behalf of the production of recombinant proteins the final choice of the production organisms will depend on economic parameters such as the culturing, growth and purification costs. Till now plants have not been used for the production of proteins, although they represent a cheap source of biomass. Production of heterologous proteins in plants can be a cheap alternative to the use of microorganisms, especially in those cases where the extraction of the protein can be fitted into an existing industrial process. The costs of growing modified plants are low in comparison with the costs of fermentation of microorganisms or animal cell cultures, and even neglectable, when the plant is already used for the production of bulk vegetable substances. The starch industry (maize, tapioca, potato, cassava) is particularly suitable for co-production of heterologous proteins, because the first steps of the existing procedure of the starch extraction do not involve denaturing conditions. The protein fraction is held in solution in the extracted cell juice at low temperatures. This protein-rich juice stream is a waste product of the starch industry and is, especially for environmental reasons, only processed to animal fodder. To introduce a protein-purification step, the starch extraction process requires no, or hardly any, modification; consequently, due to the introduction of commercially interesting, heterologous proteins in this juice stream a very cheap source of such proteins is obtained. In addition, this preferred embodiment of the invention augments the economic value of the waste stream. Obviously, for proteins with a high economic value, a similar production method can be applied on a smaller scale and starch production be of secondary importance.

In a broad sense, the invention thus provides a process for the production in a plant host of heterologous protein material which is to be excreted from the cells in which it is produced, by growing plants or plant cells that, by means of genetic manipulation, optionally of an ancestor, using a recombinant polynucleotide, have been provided with the genetic information which is required to allow the plant host to express the heterologous protein material and excrete it from the cells in which it is formed, the genetic information introduced into the host comprising an expression cassette that is functional in the host cell and contains at least a gene coding for the mature protein material, directly preceded by genetic information coding for a plant signal peptide that is functional in the host.

Preferred, according to the invention, is a process in which a protein material is produced that, in its natural environment, originates from a precursor which contains a signal peptide that provides for excretion from the cell and which itself is cleaved off, the genetic information introduced into the plant host comprising an expression cassette which is functional in the host and contains a gene construct comprising the gene encoding the mature protein material and, directly preceding it, genetic information coding for a plant signal peptide that is functional in the host, instead of the genetic information coding for the natural signal peptide of the heterologous protein material.

The expression 'protein material' refers to material such as polypeptides and proteins, whether or not glycosylated. The expression 'heterologous protein material' refers to protein materials that are foreign to the selected plant host, e.g. are naturally not produced in this host. Although the heterologous protein material to be produced can in principle be from plant origin, or even originate from yeast, the invention is focussed in particular on the use of a plant host for the production of animal or human protein materials, especially the more complex proteins that require one or more post-translational processing steps. Consequently, according to the invention, it is preferred that the protein material produced be an animal or human protein which requires one or more post-translational processing steps, including at least an excretion from the cells in which the protein is produced in the form of a precursor containing a signal peptide preceding the mature protein, and a cleavage of this signal peptide. In a particularly preferred embodiment of the invention the protein material produced is human serum albumine.

The words 'optionally of an ancestor' refer to the fact that plants are living beings, which implies that the genetic information required for production of the heterologous protein material, introduced into the first transgenic plants or plant cells, e.g. the first generation of the manipulated plants, may also be present in the progeny. Obviously, also these and later generations of the transgenic plants and plant cells may be used for the production of heterologous protein material.

The words 'recombinant polynucleotide' indicate DNA and RNA constructs that are the result of techniques as such known in recombinant DNA technology. Presently, most transformation methods are based on the use of recombinant DNA, for example in the form of plasmids, so that the recombinant polynucleotide to be used preferably consists of recombinant DNA, but the invention is not limited thereto and, consequently, also covers methods of genetic manipulation in which recombinant RNA is put into practice.

The expression 'expression cassette' is conventional and refers to a combination of regulatory elements that are required by the host for the correct transcription and translation (expression) of the genetic information contained in the expression cassette. These regulatory elements comprise a suitable (i.e. functional in the selected host) transcription promoter and a suitable transcription termination sequence.

As was mentioned before, according to the invention it is preferred, that the genetic information introduced into the plant host comprises an expression cassette that is functional in the host and contains a gene construct comprising a gene encoding the mature protein material and, directly preceding it, genetic information coding for a plant signal peptide that is functional in the host and is derived from the pathogenesis-related protein PROB12. This plant signal peptide proved in different plant species to accomplish a correct excretion from the cell, a correct cleavage of the signal peptide and a correct folding of the mature protein material.

With respect to the nature of the host, the invention, in principle, does not impose any limitations other than practical limitations of temporary character, related to the fact that methods for the transformation of certain plant species have not been developed yet. In a very special preferred embodiment of the invention a plant that is suitable for the production of starch is used as a host. In relation to this, one should think in the first place of plants selected from the group consisting of potato, maize, and cassava. According to the invention it is especially preferred, that the plant host used is a potato variety suitable for industrial starch production and that its tubers are used for both the extraction of starch and the production of the heterologous protein material.

According to the invention, it is also possible to use plant cells in suspension culture as the plant host. Plant cell suspension cultures are known per se. According to the invention it is very useful to use a suspension culture of plant cells of the plant species tobacco as the plant host.

In the experimental part some specific Examples according to the invention are given. These Examples are 1) a process for the production of human serum albumine by growing potato plants that, by means of genetic manipulation, optionally of an ancestor, using a recombinant polynucleotide, have been provided with the genetic information required to allow expression and correct post-translational processing of the human serum albumine by the potato plants, the genetic information introduced into the potato comprising an expression cassette that is functional in the potato and contains at least a gene coding for human serum albumine, directly preceded by genetic information coding for a plant signal peptide that is functional in the potato and is derived from the pathogenesis-related protein PROB12, and extracting the human serum albumine produced from the genetically manipulated potato tubers, and 2) a process for the production of human serum albumine by growing in suspension cells of the plant species tobacco that, by means of genetic manipulation, optionally of an ancestor, using a recombinant polynucleotide, have been provided with the genetic information required to allow the suspended tobacco cells to express and correctly post-translationally process the human serum albumine, the introduced genetic information comprising an expression cassette suitable for expression in tobacco and containing at least a gene coding for mature human serum albumine, directly preceded by genetic information encoding a plant signal peptide that is functional in tobacco and is derived from the pathogenesis-related protein PROB12, and extracting from the culture medium the human serum albumine produced by the genetically manipulated, suspended tobacco cells.

More in particular, the experimental part shows, that cells derived from potato or tobacco plants have been transformed using a vector containing a marker gene for kanamycin selection, as well as a gene coding for human serum albumin (HSA), preceded by either the natural HSA signal sequence (for comparison), or the signal sequence of a plant pathogenesis-related protein. Also, electroporation experiments were carried out on protoplasts of tobacco plants. These experiments aimed at obtaining an excretion of HSA across the plasma membrane of the transgenic plant cells. During the excretion process, the HSA protein is modified to a form in which the protein obtains its physiological function.

After transformation, expression has been demonstrated in all the investigated plant parts (potato: leafs, stem, stalks and tubers, the latter both fresh as well as after 2 weeks of storage at 4° C. as is usual with industrial potato's; tobacco: leafs, callus and suspension cells). Excretion of HSA by transgenic cells was proven with three methods:

a) after electroporation of tobacco protoplasts with chimaeric HSA-gene constructs, HSA could specifically be detected in the culture medium using Western blotting. In extracts of the transgenic tobacco protoplasts no HSA could be detected.

b) callus (undifferentiated cell material) was derived from HSA-transgenic tobacco plants. With this callus a suspension culture was set up. In extracts of tobacco suspension cells no HSA protein could be detected.

c) After transformation of potato with the constructs mentioned above and after regeneration of adult potato plants, HSA could be detected with high specific concentration in the extracellular fluid isolated from transgenic leaf material. The extraction of extracellular fluid from leaf material was monitored using cellular and extracellular marker enzymes. With all three test methods mentioned above (a, b & c) it appeared, that both the human and the plant signal peptide can lead to excretion of HSA. However, it appeared from amino acid analyses of HSA isolated from transgenic plants that only the plant signal peptide resulted in a correct processing (i.e. removal of the signal peptide at the right cleavage site).

The functioning of the heterologous constructs as described in the experimental part proves that a signal peptide of a PR-protein can establish excretion and correct processing of heterologous proteins to the extracellular space.

DESCRIPTION OF THE PREFERRED EMBODIMENTS

I Construction of chimaeric HSA-genes for the expression in plants

Figure 1:
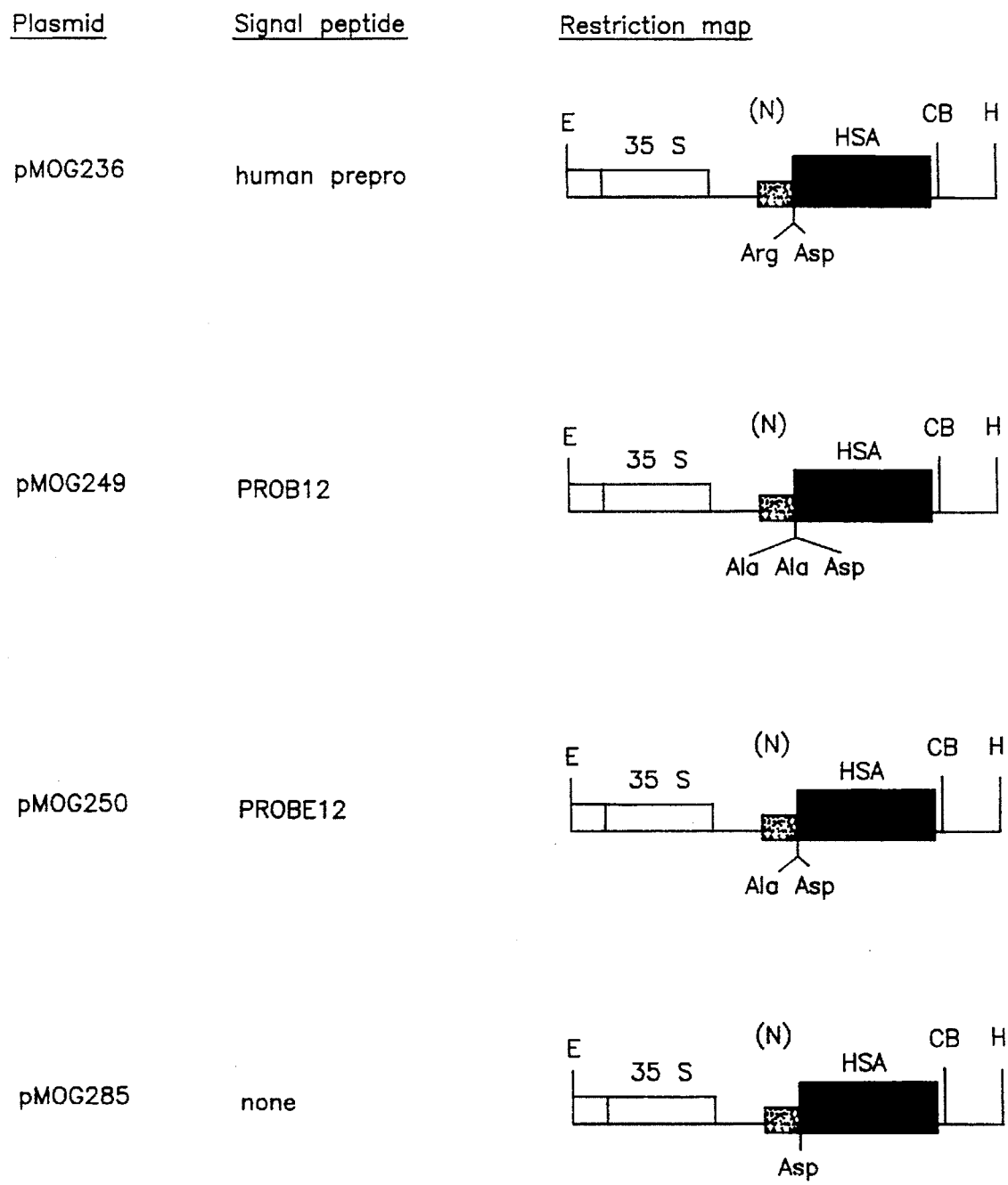
FIG. 1 A survey map of the constructs that were used for the chimaeric HSA-genes. On the schematic restriction maps are indicated, from left to right: the enhancer and promoter (2 open boxes), ALMV leader (thick line), signal sequence (dotted box), structural HSA gene (black box) and nos terminator (thin line). The restriction sites are indicated by one-character codes.

For the expression of the human gene for serum albumin (HSA) the following regulatory sequences were used:

1) The constitutive 35S promoter derived from the cauliflower mosaic virus (CaMV, Guilley et al., 1982), equipped with a double enhancer for optimal gene-expression.
2) The transcription-termination sequence derived from the gene coding for nopaline synthase (nos) of the pTiC58 plasmid from Agrobacterium tumefaciens (Bevan, 1984).
3) The 5' leader sequence of the alfalfa mosaic virus (ALMV, Brederode et al., 1980) for stabilisation of the chimaeric messenger RNA. A fusion was made between the leader sequence and the sequences coding for the HSA (FIG. 1). An overview map of the four constructs used is given in FIG. 1.

Figure 2:
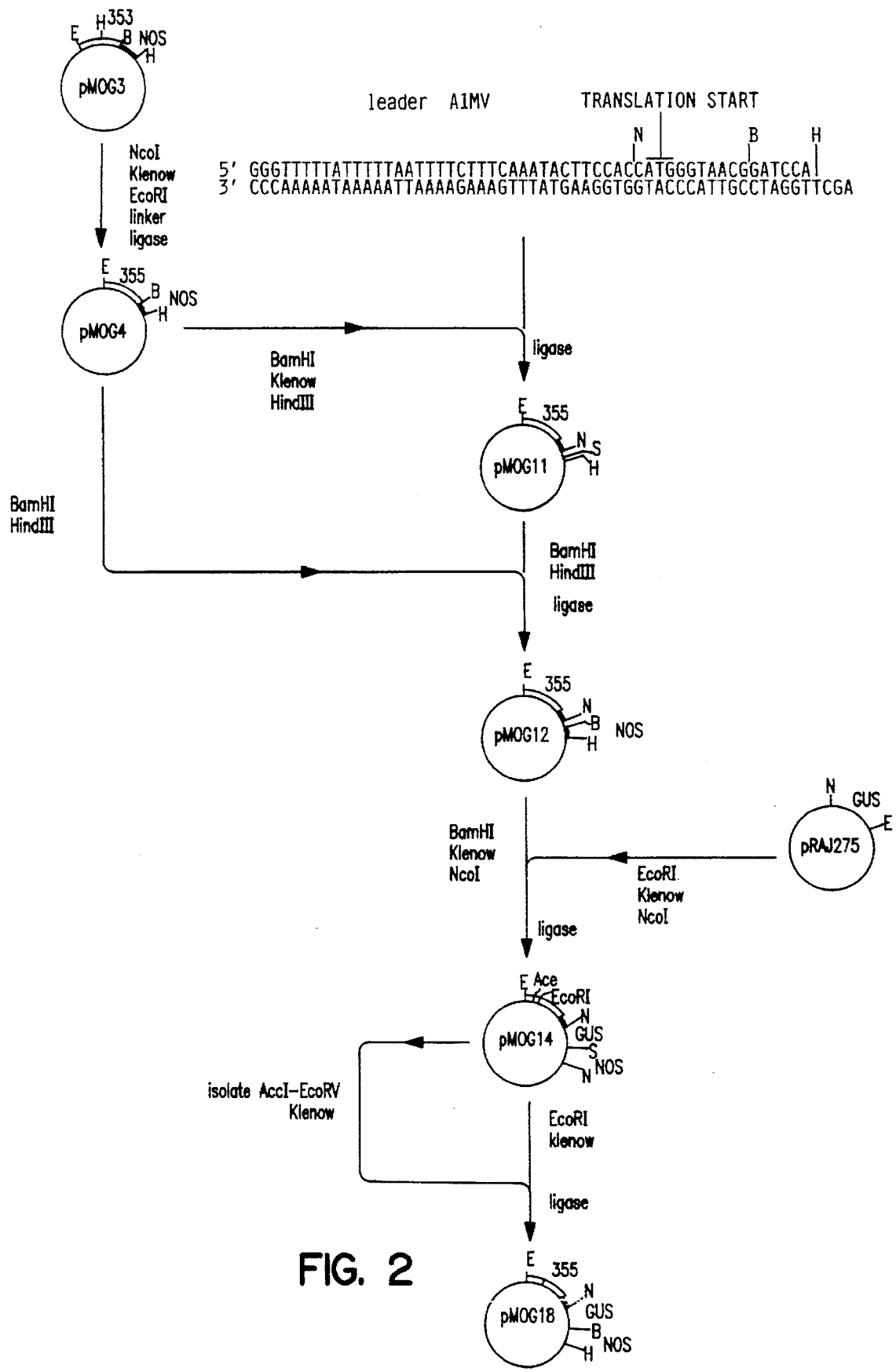
FIG. 2 (SEQ ID NO:1 and SEQ ID NO:2) Schematic outline of the construction of plasmid pMOG18. The different plasmids are not depicted in proportion.

The construction of the different plasmids via standard recombinant DNA-techniques (Maniatis et al., 1982) started from pMOG18 (FIG. 2). This plasmid is derived from E. coli vector pUC18 (Yanisch-Perron et al., 1985), which contains in the polylinker the CaMV 35S promoter/enhancer, followed by the AMV leader sequence, the gene for β-glucuronidase (Sleat et al., 1987) and the nos-terminator (Bevan, 1984). This plasmid was derived as is indicated in FIG. 2. The expression-cassette, consisting of the CaMV 35S promoter and the nos-terminator was placed in plasmid pUC18 (=pMOG3) as EcoRI-HindIII fragment (derived from plasmid pROK1; Baulcombe et al., 1986). Subsequently, the 5' proximal region of the 35S promoter was removed by blunt-ending the NcoI-site in the promoter using Klenow polymerase, and reducing the length of the plasmid, via digestion with EcoRI and insertion of the EcoRI-linker, resulting in plasmid pMOG4. The BamHI-HindIII fragment from plasmid pMOG4 was replaced with a synthetic fragment containing the leader-sequence of the alfalfa mosaic virus (ALMV). The indicated NcoI-site in the synthetic fragment is located directly downstream of the ALMV-leader and contains the ATG translation-initiation codon. In the obtained plasmid pMOG11 the BamHI-HindIII-fragment with the nos-terminator was reinserted, resulting in plasmid pMOG12. A gene coding for β-glucuronidase (derived from plasmid pRAJ275; Jefferson, 1987) was placed in plasmid pMOG12 as a NcoI-BamHI fragment, resulting in plasmid pMOG14. Finally, the enhancer sequence of the 35S promoter, located on a AccI-EcoRV fragment from pMOG14, was isolated, blunt-ended with Klenow polymerase and placed in the blunt-ended EcoRI-site of pMOG14, which resulted in plasmid pMOG18 containing a double enhancer sequence (FIG. 2).

The HSA-protein is naturally synthesized as a precursor (Judah et al., 1973), in which the mature protein of 585 amino acids is preceded by a 'prepro'-peptide of 24 amino acids. The cloned preproHSA cDNA (Lawn et al., 1981) was used as starting material for the construction of pMOG36, in which the sequence coding for the HSA-protein is preceded by the human HSA-prepro-peptide (Lawn et al., 1981). Also, the sequence coding for the mature HSA-protein was fused in two different ways to a signal peptide of plant origin (plasmids pMOG49 and pMOG50). Finally, a HSA-gene was made that did not contain a sequence coding for a signal peptide (plasmid pMOG85).

a) Construction of plasmid pMOG36, containing preproHSA

Figure 3:
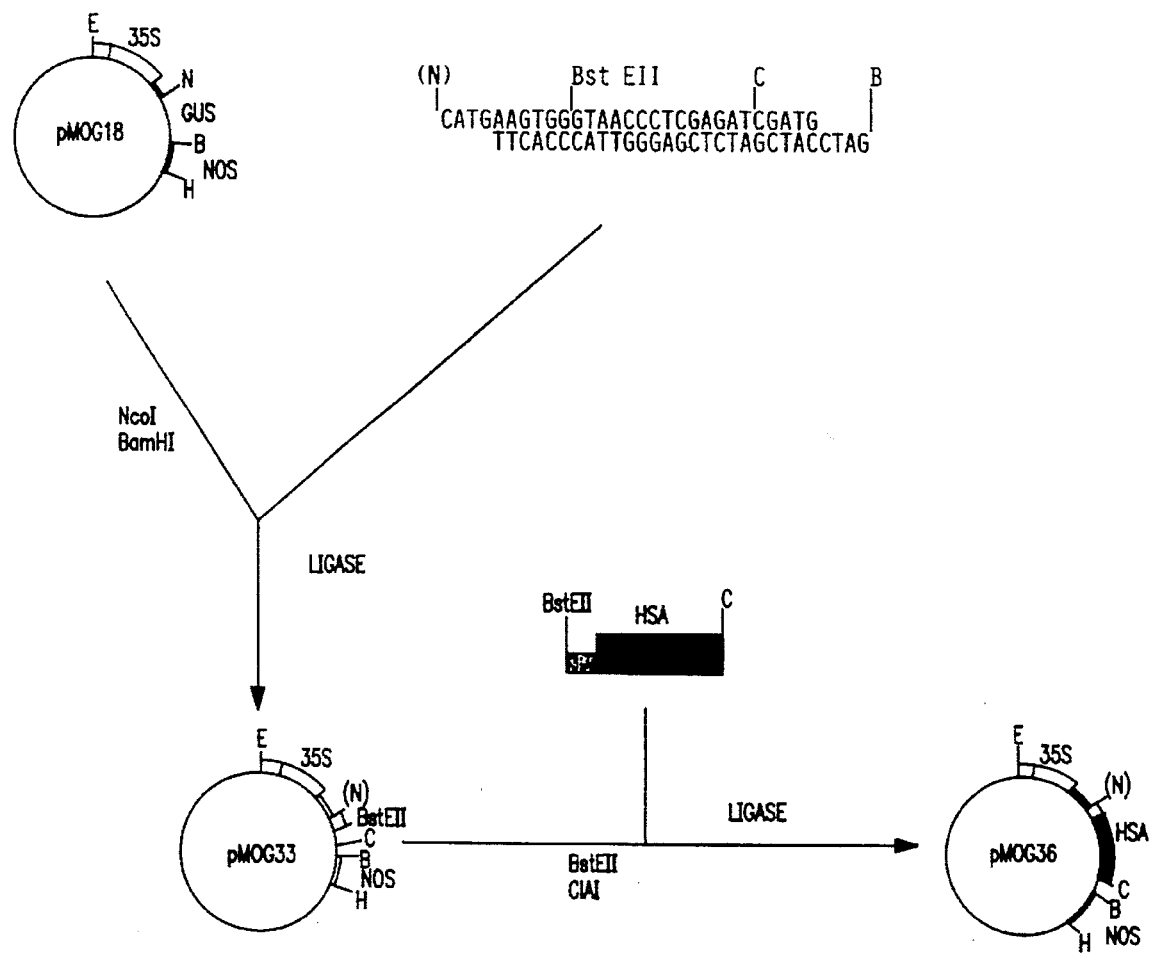
FIG. 3 (SEQ ID NO:3 and SEQ ID NO:4) Schematic outline of the construction of plasmid pMOG36. The different plasmids are not depicted in proportion.
Figure 4:
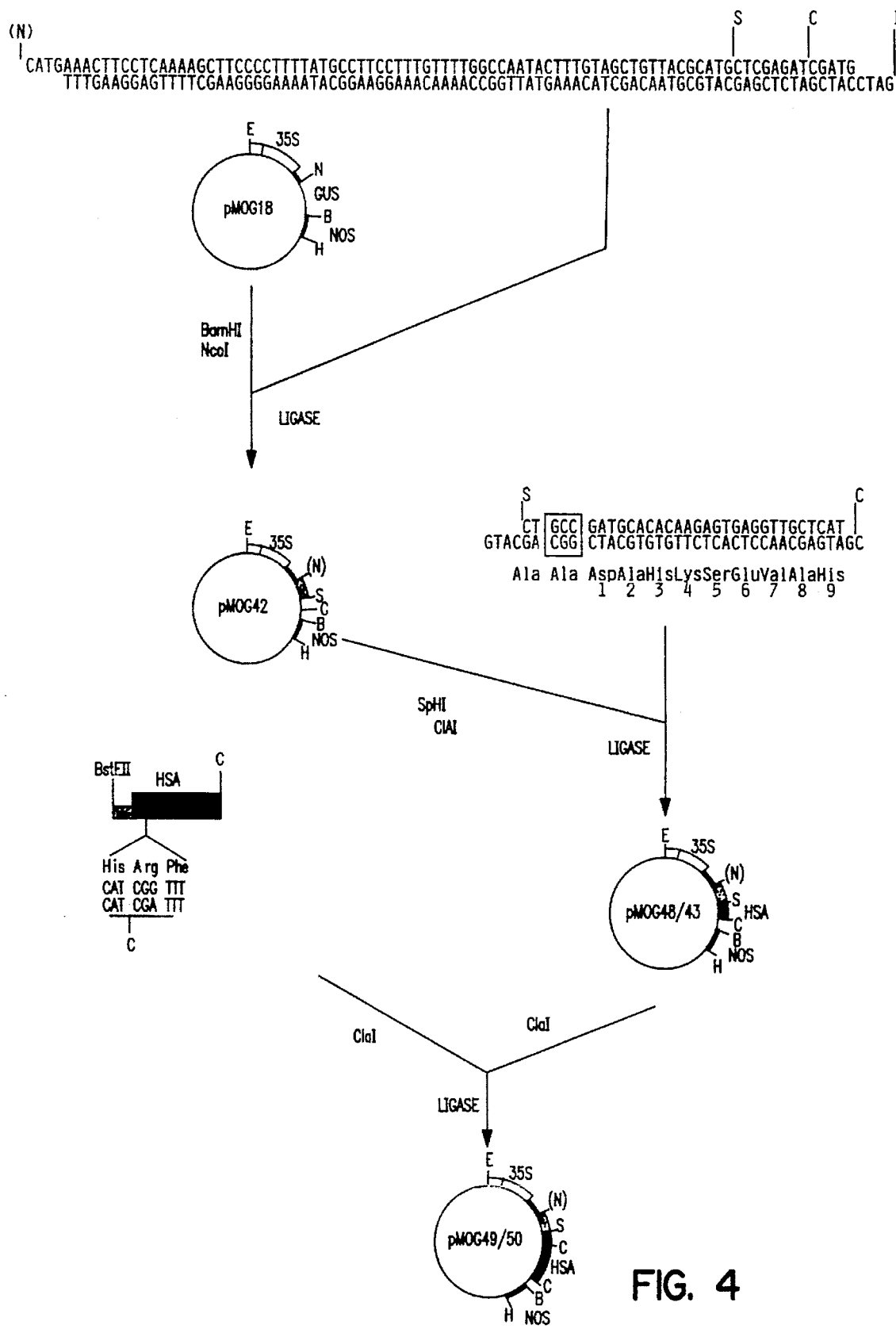
FIG. 4 (SEQ ID NO:5 through SEQ ID NO:9) Schematic outline of the construction of plasmid pMOG49 and pMOG50. The different plasmids are not depicted in proportion. The sequence in the box, which codes for an alanine-residue, has been used for the construction of pMOG48.

As is indicated in FIG. 3, the sequence coding for preproHSA was cloned as a Bst EII-ClaI-fragment. The restriction site for Bst EII (GGTAACC) is located nine nucleotides behind the start codon of the HSA gene (Lawn et al., 1981). Using standard techniques, a restriction site for ClaI was created, 27 bp behind the TAA stopcodon of the HSA-gene by mutation of the sequence TACCAT to ATCGAT, using M13-vectors (Yanisch-Perron et. al., 1985). Due to this, the Bst EII-ClaI fragment had a size of 1850 bp. A synthetic NcoI-BamHI fragment of 29 bp was placed in pMOG18. In the resulting plasmid pMOG33, directly behind the ATG startcodon, the missing 9 nucleotides till the Bst EII-site, followed by a ClaI-site, were present. In plasmid pMOG33 the preproHSA gene was placed as is indicated in FIG. 3, resulting in plasmid pMOG36.

b) Construction of the plasmids pMOG49 and pMOG50, containing a fusion of the PROB12 signal peptide to the mature HSA-protein The sequence coding for the mature HSA-protein was fused in two ways to the signal peptide of the PR-protein PROB12 from Samsun NN tobacco (Cornelissen et al., 1986). This plant signal peptide has a Length of 25 amino acids and an Ala-Ala peptide binding constitutes the cleavage-site of the signal peptide and the mature PROB12 protein. The cleavage-site of the 24 amino acid preprosequence of HSA and the mature HSA is Arg-Asp (Lawn et al. 1981). In the constructions presented here two different fusions were made between the pROB12 signal peptide and the mature HSA, viz. a fusion between the last amino acid of the PROB12 signal peptide and the start of the mature HSA (Ala-Asp), and a fusion in which the mature HSA is preceded by the cleavage-sequence of the PR-protein (Ala-Ala-Asp, FIG. 4).

For the construction of plasmids pMOG49 and pMOG50, on the 9th and the 10th codon of the mature HSA the sequence CAT CGG T was mutagenised into CAT CGA T by means of standard procedures (Kunkel, 1985) using M13-vectors (Yanisch-Perron et al., 1985). Concomitantly, a ClaI restriction site was created without changing the encoded protein (FIG. 4); the correct mutagenesis was confirmed by sequence analysis. The fusion of the plant regulatory signals started from plasmid pMOG18, in which a synthetic NcoI-BamHI fragment of 80 bp was placed, which fragment codes for the signal peptide of PROB12, from the ATG start codon till the SphI restriction-site that is located directly in front of the first Ala-residue of the cleavage-size (Cornelissen et al., 1986). In the resulting plasmid pMOG42, finally, two different synthetic linkers were placed, coding for, on the one hand, a Ala-Ala-Asp fusion with the mature HSA-gene till the created ClaI restriction-site in the 9th and 10th codon of the mature protein, on the other hand for the corresponding Ala-Asp fusion. In the resulting plasmids pMOG48 and pMOG43, subsequently, the mutagenised HSA-gene was placed as ClaI-fragment, resulting in the plasmids pMOG49 and pMOG50, respectively.

c) Construction of plasmid pMOG85, containing mature HSA

Figure 5:
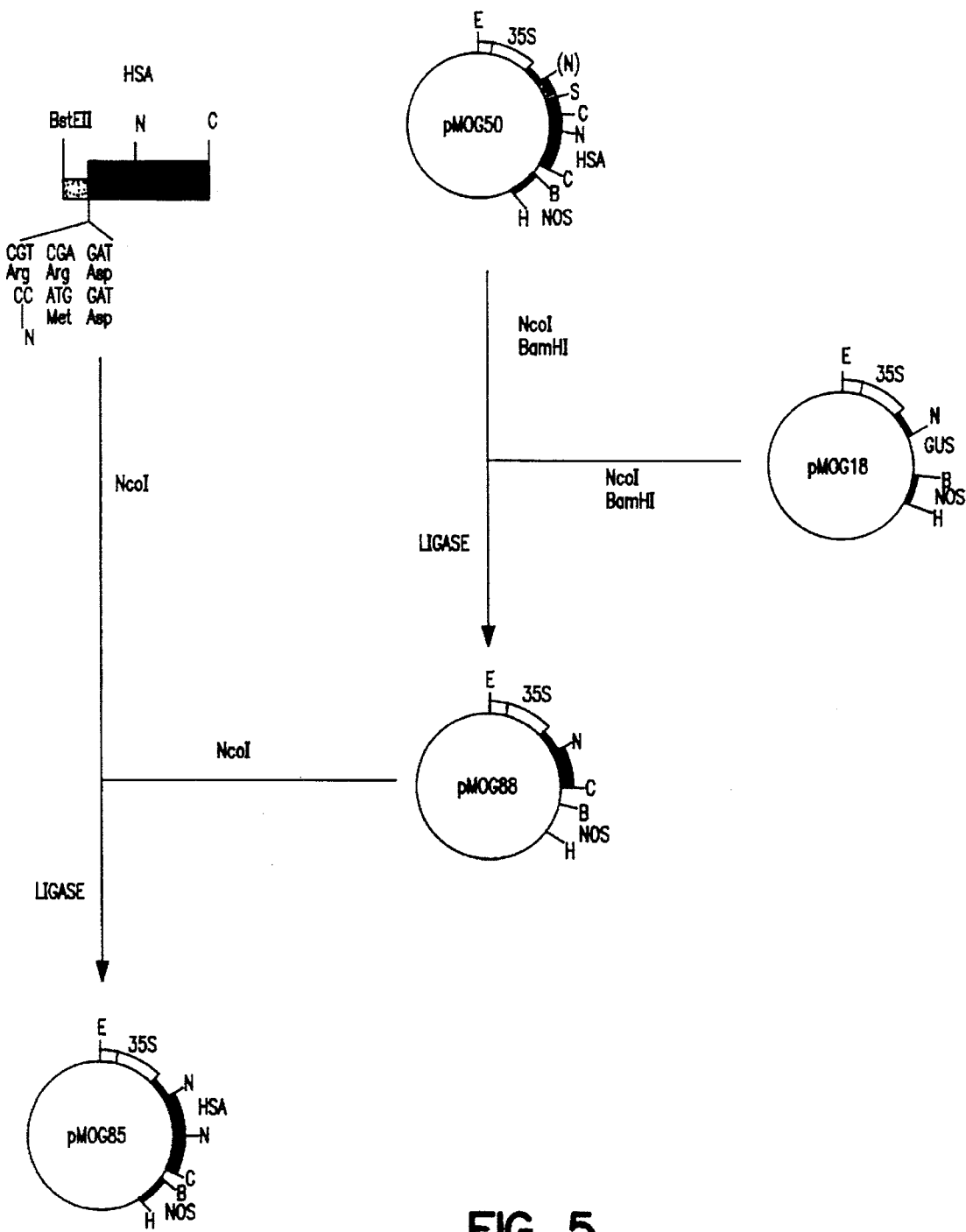
FIG. 5 Schematic outline of the construction of plasmid pMOG85. The different plasmids are not depicted in proportion.

Using standard procedures (Kunkel, 1985) the HSA-gene was mutagenised in a M13-derived vector in such a way that in the coding sequence the first amino acid of the mature protein (Asp) was preceded by a NcoI restriction-site, containing an ATG translation-start codon in the correct reading frame (FIG. 5). The HSA-gene thus derived, including the NcoI restriction-site, was checked on DNA-sequence and subsequently subcloned in plasmid pMOG18 (FIG. 5). The NcoI-BamHI fragment, containing the C-terminal region of the HSA-gene, was isolated from plasmid pMOG50 and placed in vector pMOG18, resulting in plasmid pMOG88. The first 742 bp of the HSA-gene, including the created ATG startcodon, was placed in plasmid pMOG88 as a NcoI-fragment. The resulting plasmid pMOG85 now contained the mature HSA-gene without the signal peptide sequence in the expression vector.

The plasmids pMOG36, pMOG49, pMOG50 and pMOG85 contained now the HSA-gene to be introduced as a 3.0 kb EcoRI-HindIII restriction fragment.

II Electroporation of tobacco protoplasts

The isolation and electroporation of tobacco protoplasts (Nicotiana tabacum cv. SR1) was carried out according to Rodenburg et al. (1989). For the electroporation 5×10⁵ protoplasts were suspended in 0.5 ml buffer, preincubated during 10 minutes at 0° C. in the presence of 40 µg/ml supercoiled DNA of one of the plasmids pMOG36, pMOG49, and pMOG50 and subsequently electroporated at 300 V/cm and one pulse of 38 msec. After again 10 minutes at 0° C., the cells were diluted in 5 volumes K3G medium and further grown in the dark at 20° C. The presence of the HSA-protein was tested as described in VI.

III Transformation of tobacco and induction of suspension cells

For the introduction of gene-constructs in plants, various techniques are available such as transformation with *Agrobacterium tumefaciens* or *Agrobacterium rhizogenes*, microinjection, particle bombardment, DNA-uptake in protoplasts, etc. The actual method of introduction of DNA is not critical with respect to the invention. For the transformation of tobacco, cocultivation of leaf-disks with *Agrobacterium tumefaciens* was used according to the procedure of Horsch et al. (1985). This method is based on the principle of the binary vector system (Hoekema et al., 1983), in which *Agrobacterium* strains are used that on the one hand contain a plasmid, on which the virulence (vir) genes are located and on the other hand, a plasmid compatible with it, that contains the gene to be introduced. The four relevant gene-constructs as they are present on the plasmids pMOG36, pMOG49, pMOG50 and pMOG85 were cloned in the binary vector pMBV4. This vector can replicate both in *E. coli* and in *Agrobacterium*, is derived from the binary vector Bin19 (Bevan, 1984) and does not differ from it on points that are essential for the present invention. Vectors pMBV4 and Bin19 contain between the left and the right border sequence of the T-DNA an identical chimaeric NPTII-gene encoding kanamycin-resistance (Bevan, 1984), as well as a so-called polylinker for the cloning of the construct to be integrated. The chimaeric HSA-genes located on the plasmids pMOG36, pMOG49, pMOG50 and pMOG85 were placed in the polylinker of the vector pMBV4 as a 3.0 kb EcoRI-HindIII-fragment, after the vector was linearised with EcoRI and HindIII. The binary plasmids thus obtained, respectively pMOG236, pMOG249, pMOG250 and pMOG285 were now, by means of mobilisation using the plasmid pRK 2013 (Ditta et al., 1980), transferred to an *Agrobacterium* strain, containing a plasmid carrying the vir-genes for the transfer of the T-DNA to the plant.

Using the *Acrobacterium* strains thus obtained, transformation of tobacco was carried out. Transgenic plants were regenerated from shoots that developed on selection-medium (100 mg/l kanamycin). The presence of HSA-protein was tested as described hereafter, in VI. A suspension culture was initiated from the transgenic plants that showed the highest expression level (clone pMOG249#1). To this end, callus was induced on transgenic leaf disks by growing on MS medium, 3% sucrose (MS30), 2.0 mg/l NAA, 0.1 mg/l kinetine and 50 mg/l kanamycin, after which the callus was transferred to liquid medium of the same composition. Afer one week in suspension, the medium was replaced with new MS30, now containing 0.5 mg/l 2.4-D. This medium was refreshed every week till a homogeneous culture had been obtained. From the 7th week onwards the kanamycin selection was increased in steps of 25 mg/l to 100 mg/l.

IV Transformation of potato

For the transformation of potato, the binary vector system was used, developed for *Agrobacterium tumefaciens* as described above under III. Tuber-disks of the cultivar Desiree were cocultivated with the *Agrobacterium* strains containing the plasmids pMOG236, pMOG249 or pMOG250, via the method described by Hoekema et al., (1989). In total, 75 transgenic plants were regenerated from shoots that had developed on selection medium (100 mg/l kanamycin), viz. 51 plants with construct pMOG236, 12 with pMOG249 and 12 with pMOG250. The transgenic plants were multiplied in vitro, after which they were grown in pot soil into adult plants for analyses.

V Detection of HSA-mRNA and HSA-protein

All transgenic potato plants were tested for the presence of HSA-mRNA (Verwoerd et al., 1989) using Northern blotting. In 46 of the 51 pMOG236, 10 of the 12 pMOG250 and all pMOG249 transgenic plants, HSA-mRNA was detected.

The presence of HSA-protein was tested by separating the soluble protein fraction on 7.5–15% SDS-polyacrylamide gradient gels, followed by Western blotting on nitrocellulose and immunodetection with goat-antiHSA (Sera-Lab, USA) followed by rabbit-anti-goat peroxidase. The binding conditions during the incubation of nitrocellulose with antibodies were 10 mM NaPi, pH 7.2, 150 mM NaCl, 1.25% Blotto, 0.2% Tween 20, 0.1% Triton X100, 35° C. HSA was visualized with a peroxidase staining with o-dianisidine. Detectable amounts of HSA were found in 31 pMOG236, 8 pMOG249 and 9 pMOG250 plants, namely in leafs, stems and tubers.

VI Excretion of HSA by plant cells

After transformation, both synthesis and excretion of HSA by transgenic plants could be shown. It appeared, that each of the signal peptides used was capable of excreting HSA from the plant cell. Excretion could be shown in three ways:
a) Following electroporation of tobacco protoplasts with the above mentioned vectors and subsequent transient expression of the introduced gene and signal sequence, HSA could be specifically detected in the culture medium after a culture period of 48 hours, using Western blotting. To this end, the medium was desalted on a PD10/G25 column and concentrated by freeze-drying. In extracts of transgenic tobacco protoplasts (after lysis of the pelleted protoplasts in 2× concentrated SDS-sample buffer) the HSA was below the detection level (<1 ng HSA/25 µg soluble protein).
b) In the medium of suspension cells of transgenic tobacco, HSA could be detected using Western blotting (2 ng/10 µg extracellular protein). In extracts of pelleted suspension cells the HSA level was on the detection level of 1 ng HSA/25 µg soluble protein.
c) Through analysis of the extracellular fluid in transgenic leaf material of potato plants. It appeared possible to extract extracellular fluid after vacuum-filtration of leaf slices in 5 mM Hepes, pH 6.3, 50 mM NaCl, followed by slow centrifugation (600 g) (Hendriks et al., 1985). This fluid could be identified as such by determination of the specific activity of the marker enzymes glucose-6P dehydrogenase (cytoplasmatic) and peroxidase. According to the Western blotting analysis, it appeared that the extracellular fluid contained approximately a 20× higher HSA-concentration (per mg protein) than a total leaf extract. From leafs of transgenic tobacco plants with the construct pMOG285, containing the HSA-gene without signal peptide, the extracellular fluid was extracted as described for potato plants. In this fluid no HSA could be detected.

VII In vivo processing of HSA

To investigate whether HSA was processed correctly during the transport through the plant cell, during which the corresponding signal peptide has to be cleaved off in front of the Asp-codon of mature HSA (FIG. 1), various experiments were carried out. Since HSA has no enzymatic function, only physical properties could be analysed, whereby plant HSA could be compared with standard HSA (the analysis procedures used are described in detail in VIII–X):
a) the molecular weight was compared using FPLC-gel filtration and SDS-PAGE (7.5–15% gradient gels).
b) The elution pattern during a salt gradient on monoQ anion exchanger (0–>350 mM NaCl in 50 mM Tris pH 8.0).
c) CNBr digestions of purified HSA were analysed on 20–27% SDS-PAGE gradient gels after silver staining.
d) amino acid sequence of HSA purified from transgenic plants.

The only differences that could be found consisted of differences in the N-terminal amino acid sequence, depending on the signal peptide used (see IX), and differences in the CNBr-digestion pattern.

VIII Purification of HSA from transgenic potato plants

From the clones with the highest expression, one from each construct (236#31, 249#10 and 250#6), enough transgenic plants were grown for the extraction of HSA. For this purpose 500–1000 gram plant material was homogenised in 10 mM NaPi pH 7.2, 150 mM NaCl (PBS) with 0.6% PVPP, 0.1 mM PMSF, 1 mM EDTA at 4° C. The soluble fraction was freed from cell debris and incubated with anti-HSA coupled to 1.5 ml Reactigel HF-65 (Pierce Chemicals) and 0.5% Tween 80, during 4 hours. The HSA-anti-HSA-Reactigel Complex was isolated by centrifugation, transferred to a 2ml column and rinsed twice with 0.5% Tween 80 in PBS. Desorption of HSA was carried out by elution with 0.1M glycine, pH 2.5, 10% dioxan, after which the buffer was quickly exchanged by 50 mM Tris, pH 8.0 using a PD10/G25 column (Pharmacia). The eluate was directly filtered (0.22 µM) and transferred to a MonoQ column (HR5/5 Pharmacia). By means of a linear gradient (0 to 350 mM NaCl in 50 mM Tris/HCl pH 8.0 in 20 minutes, 1 ml/min) HSA was for the most part purified from the aspecifically bound protein components. The fractions that appeared to have a high concentration of HSA in a Western blot, were concentrated by freeze-drying and loaded on HR10/30 Superose 6 gel filtration column (Pharmacia) in PBS. The elution volume of HSA isolated from transgenic plants corresponded exactly with the elution volume of standard HSA, in both columns. The purity of the isolated HSA was confirmed with a silver-stained SDS-gel.

IX N-terminal amino acid sequence of HSA from transgenic plants

The HSA-peak of the Superose 6 gel filtration column (VIII) was directly spotted on Immobilon PVDF membrane for amino acid sequence analysis using an Applied Biosystems 477A Protein Sequencer (Eurosequence B. V., Groningen). Unexpectedly, only HSA from pMOG250 plants appeared to have been correctly processed; the amino acid sequence at the N-terminus of purified HSA was established as Asp-Ala-His-Lys-Ser-Glu (SEQ ID NO:10). This sequence fully represents the N-terminal sequence of correctly processed HSA, present in human blood plasma (Lawn et al., 1981).

The amino acid sequence of the N-terminus of HSA, purified from pMOG236 plants (i.e. the construct with the human signal peptide) demonstrated that the excreted HSA still contained a propeptide: Arg-Gly-Val-Phe-Arg-Arg (SEQ ID NO:11). Only the prepeptide of 18 amino acids had been cleaved off. In humans, the propeptide is cleaved off during a late phase of the excretion process, by means of a serine protease (Brennan et al. 1984). This class of proteinases is rare in plants (Ryan & Walker-Simmons, 1981).

HSA, purified from transgenic plants pMOG249, appeared chemically blocked for Edman-degradation at the N-terminus, possibly due to the presence of the Ala-residue (Persson et al., 1985) which originates from the signal peptide construct that was used (cf. FIG. 1).

X Cyanogen bromide digestion of HSA from transgenic plants

Purified HSA (VIII) on PVDF membrane was used as starting material for CNBr digestion. The desorption from the membrane was carried out with 50 mM Tris/HCl, pH9, 2% SDS, 2% Triton X100, followed by cold acetone precipitation. The dried pellet was resuspended in 10 µl 70% formic acid with 200 nmol CNBr/µg protein and incubated at room temperature during 24 hours. After dilution, the digest was freeze-dried and analysed on 20–27% SDS-PAGE according to Giuilan et al., (1983). In this experiment it appeared, that only the digest derived from HSA, isolated from transgenic pMOG236, showed a deviant pattern in comparison with the digest of the standard HSA. Very likely, this is a result of the presence of the propeptide preceding the HSA, as appeared from the amino acid sequence data (see IX).

REFERENCES

Baulcombe, Saunders, Bevan, Mayo, Harrison (1986) Nature 321, 446–449
Bevan (1984) Nucl Acid Res 12, 8711–8721
Bherens, Spiekerman, Brown (1975) Fed Proc 34, 591
Brederode, Koper-Zwarthoff, Bol (1980) NAR 8, 2213–2223
Brennan, Owen, Boswell, Lewis, Carrell (1984) Biochem Biophys Acta 802, 24–28

Carlson, Botstein (1982) Cell 28, 145–154
Chen, Varner (1985) EMBO J 4, 2145–2151
Cornelissen, Hooft van Huijsduijnen, Bol (1986) Nature 321, 531–532
Della-Cioppa, Kishore, Beachy, Fraley (1987) Plant Physiol 84, 965–968
De Loose, Alliotte, Gheysen, Gielen, Soetaert, Van Montagu, Inze (1988) Gene 70, 13–23
Ditta, Stanfield, Corbiu, Helinski (1980) Proc Nat Acad Sci, USA 77, 7347–7351
Dorel, Voelker, Herman, Chrispeels (1989) J Cell Biol 108, 327–337
Etcheverry, Forrester, Hitzeman (1986) Bio/Techn 4, 726–730
Giuilan, Moss, Greaser (1983) Anal Biochem 129, 277–287
Goodman, Knauf, Houck, Comai (1987) PCT/WO 87/00865
Guilley, Dudley, Jonard, Balazs, Richards (1982) Cell 30, 763–773
Harkki, Uusitalo, Bailey, Penttila, Knowles (1989) Bio/Techn 7, 596–603
Hendriks, Van den Berg, Schram (1985) Planta 164, 89–95
Herskowitz, Oshima (1982) in: The molecular biology of the yeast Saccharomyces Vol. 1, 181–210
Hoekema, Hirsch, Hooykaas, Schilperoort (1983) Nature 303, 179–180
Hoekema, Huisman, Molendijk, Van den Elzen, Cornelissen (1989) Bio/Techn 7, 273–278
Hooft van Huijsduijnen, Cornelissen, Van Loon, Van Boom, Tromp, Bol (1985) EMBO J 4, 2167–2171
Horsch, Fry, Hoffmann, Wallroth, Eichholtz, Rogers, Fraley (1985) Science 225, 1229–1231
Jefferson (1987) Plant Mol Biol Report 5, 387–405
Johnsson, Bankaitis, Emr (1987) Cell 48, 875–885
Judah, Gamble, Steadman (1973) Biochem J 134, 1083–1091
Kingsman, Kingsman, Mellor (1987) Trends in Biotechn 5, 53–56
Kornfeld (1987) Fed Am Soc Exp Biol J 1, 462–468
Kunkel (1985) Proc Nat Acad Sci. USA 82, 488–492
Latta, Knapp, Sarmientos, Brefort, Becquart, Guerrier, Jung, Mayaux (1987) Bio/Techn 5, 1309–1314
Lawn, Adelman, Bock, Franke, Houck, Najarian, Seeburg, Wion (1981) Nucl Acid Res 9, 6103–6114
Maniatis, Fritsch, Sambrook (1982) Molecular Cloning, Cold Spring Harbour Lab
Memelink (1988) Altered gene expression in T-DNA transformed tobacco tissues. Thesis, Rijksuniversiteit Leiden
Misra (1989) Plant Physiol 89, S47
Persson, Flinta, Heijne, Jörnval (1985) Eur J Biochem 152, 523–527
Pfeffer, Rothman (1987) Ann Rev Biochem 56, 829–852
Rodenburg, De Groot, Schilperoort, Hooykaas (1989) Plant Mol Biol (submitted)
Ryan, Walker-Simmons (1981) Plant Proteinases. In: The Biochemistry of Plants, Stumpf, Conn (eds) Acad Press, New York
Saunders, Guyer (1987) EP-A-0229712
Sleat, Gallie, Jefferson, Bevan, Turner, Wilson (1987) Gene 217, 217–225
Stetler, Forsyth, Gleason, Wilson, Thompson (1989) Bio/Techn 7, 55–60
Verwoerd, Dekker, Hoekema (1989) Nucl Acid Res 17, 2362
Yanisch-Perron, Vieira, Messing (1985) Gene 33, 103–119

---

We claim:

1. A process for the production in a plant host of Human Serum Albumin (HSA) by growing transgenic plants or transgenic plant cells which comprise in their genome a recombinant DNA sequence comprising in sequence;
   - a 5' non transcribed regulatory region and a 5' non translated region functional to express DNA in plants,
   - an open reading frame encoding a protein precursor comprising a plant signal peptide portion and a mature HSA-portion, and
   - a 3+ transcriptional termination region functional in plants, thereby causing the recombinant DNA to be expressed in the form of the protein precursor which is processed in the plant host's cells by cleavage of the plant signal peptide portion at or near the signal peptide-protein junction to yield the mature or substantially mature HSA-portion which is then excreted from said plant host's cells.

2. The process of claim 1 wherein the plant host is an angiosperm.

3. The process of claim 2 wherein the plant host is a dicot.

4. The process of claim 3 in which the plant host is suitable for the production of starch.

5. The process of claim 1 in which the host plant is selected from the group consisting of potato and maize.

6. The process of claim 1 in which said 5' nontranslated region is derived from PROB12.

7. The process of claim 1 in which the plant host is selected from the group consisting of *Nicotiana* species.

8. The process of claim 1 in which the 5' nontranscribed regulatory region comprises the 35S promoter derived from the cauliflower mosaic virus.

9. The process of claim 1 wherein the signal peptide-protein junction is Ala-Asp.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 54 base pairs
( B ) TYPE: nucleic acid
( C ) STRANDEDNESS: single
( D ) TOPOLOGY: linear ( x i ) SEQUENCE DESCRIPTION: SEQ ID NO:1:

GGGTTTTAT TTTAATTTT CTTTCAAATA CTTCCACCAT GGGTAACGGA TCCA    54

( 2 ) INFORMATION FOR SEQ ID NO:2:

( i ) SEQUENCE CHARACTERISTICS:
( A ) LENGTH: 58 base pairs
( B ) TYPE: nucleic acid
( C ) STRANDEDNESS: single
( D ) TOPOLOGY: linear ( x i ) SEQUENCE DESCRIPTION: SEQ ID NO:2:

AGCTTGGATC CGTTACCCAT GGTGGAAGTA TTTGAAAGAA AATTAAAAAT AAAAACCC    58

( 2 ) INFORMATION FOR SEQ ID NO:3:

( i ) SEQUENCE CHARACTERISTICS:
( A ) LENGTH: 29 base pairs
( B ) TYPE: nucleic acid (C) STRANDEDNESS: single
(D) TOPOLOGY: linear (xi) SEQUENCE DESCRIPTION: SEQ ID NO:3:

CATGAAGTGG GTAACCCTCG AGATCGATG    29

(2) INFORMATION FOR SEQ ID NO:4:

(i) SEQUENCE CHARACTERISTICS:
(A) LENGTH: 29 base pairs
(B) TYPE: nucleic acid
(C) STRANDEDNESS: single
(D) TOPOLOGY: linear (xi) SEQUENCE DESCRIPTION: SEQ ID NO:4:

GATCCATCGA TCTCGAGGGT TACCCACTT    29

(2) INFORMATION FOR SEQ ID NO:5:

(i) SEQUENCE CHARACTERISTICS:
(A) LENGTH: 88 base pairs
(B) TYPE: nucleic acid
(C) STRANDEDNESS: single
(D) TOPOLOGY: linear (xi) SEQUENCE DESCRIPTION: SEQ ID NO:5:

CATGAAACTT CCTCAAAAGC TTCCCCTTTT ATGCCTTCCT TTGTTTTGGC CAATACTTTG    60

TAGCTGTTAC GCATGCTCGA GATCGATG    88

(2) INFORMATION FOR SEQ ID NO:6:

(i) SEQUENCE CHARACTERISTICS:
(A) LENGTH: 88 base pairs
(B) TYPE: nucleic acid
(C) STRANDEDNESS: single
(D) TOPOLOGY: linear (xi) SEQUENCE DESCRIPTION: SEQ ID NO:6:

GATCCATCGA TCTCGAGCAT GCGTAACAGC TACAAAGTAT TGGCCAAAAC AAAGGAAGGC    60

ATAAAGGGG AAGCTTTTGA GGAAGTTT    88

(2) INFORMATION FOR SEQ ID NO:7:

(i) SEQUENCE CHARACTERISTICS:
(A) LENGTH: 32 base pairs
(B) TYPE: nucleic acid
(C) STRANDEDNESS: single
(D) TOPOLOGY: linear (xi) SEQUENCE DESCRIPTION: SEQ ID NO:7:

CTGCCGATGC ACACAAGAGT GAGGTTGCTC AT    32

(2) INFORMATION FOR SEQ ID NO:8:

(i) SEQUENCE CHARACTERISTICS:
(A) LENGTH: 38 base pairs
(B) TYPE: nucleic acid
(C) STRANDEDNESS: single
(D) TOPOLOGY: linear (xi) SEQUENCE DESCRIPTION: SEQ ID NO:8:

CGATGAGCAA CCTCACTCTT GTGTGCATCG GCAGCATG    38

(2) INFORMATION FOR SEQ ID NO:9:

(i) SEQUENCE CHARACTERISTICS:

(A) LENGTH: 11 amino acids
(B) TYPE: amino acid
(C) STRANDEDNESS: single
(D) TOPOLOGY: linear (xi) SEQUENCE DESCRIPTION: SEQ ID NO:9:

Ala Ala Asp Ala His Lys Ser Glu Val Ala His
1               5                   10

(2) INFORMATION FOR SEQ ID NO:10:

(i) SEQUENCE CHARACTERISTICS:
(A) LENGTH: 6 amino acids
(B) TYPE: amino acid
(C) STRANDEDNESS: single
(D) TOPOLOGY: linear (xi) SEQUENCE DESCRIPTION: SEQ ID NO:10:

Asp Ala His Lys Ser Glu
1               5

(2) INFORMATION FOR SEQ ID NO:11:

(i) SEQUENCE CHARACTERISTICS:
(A) LENGTH: 6 amino acids
(B) TYPE: amino acid
(C) STRANDEDNESS: single
(D) TOPOLOGY: linear (xi) SEQUENCE DESCRIPTION: SEQ ID NO:11:

Arg Gly Val Phe Arg Arg
1               5